(12) United States Patent
Dittrich (10) Patent No.: US 10,471,206 B2
(45) Date of Patent: Nov. 12, 2019

(54) NEEDLE INTERFACE

(71) Applicant: Sanofi-Aventis Deutschland GMBH, Frankfurt am Main (DE)

(72) Inventor: Marcus-Meinolf Dittrich, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 155 days.

(21) Appl. No.: 15/536,380

(22) PCT Filed: Dec. 14, 2015

(86) PCT No.: PCT/EP2015/079608
§ 371 (c)(1),
(2) Date: Jun. 15, 2017

(87) PCT Pub. No.: WO2016/096738
PCT Pub. Date: Jun. 23, 2016

(65) Prior Publication Data
US 2017/0348480 A1    Dec. 7, 2017

(30) Foreign Application Priority Data

Dec. 19, 2014 (EP) ..................................... 14199393

(51) Int. Cl.
*A61M 5/162* (2006.01)
*A61J 1/14* (2006.01)
(Continued)

(52) U.S. Cl.
CPC ............ *A61M 5/162* (2013.01); *A61J 1/1406* (2013.01); *A61J 1/1481* (2015.05); *A61J 1/1487* (2015.05);
(Continued)

(58) Field of Classification Search
CPC .. A61M 2039/0238; A61M 2039/0244; A61M 39/0208; A61M 5/32; A61M 5/34;
(Continued)

(56) References Cited

U.S. PATENT DOCUMENTS 4,464,178 A * 8/1984 Dalton ............... A61M 39/0208
128/DIG. 26
4,784,646 A * 11/1988 Feingold ........... A61M 39/0208
604/175
(Continued)

FOREIGN PATENT DOCUMENTS

CN    103393538    11/2013
JP    2002-119589   4/2002

OTHER PUBLICATIONS

International Search Report and Written Opinion in International Application No. PCT/EP2015/079608, dated Feb. 22, 2016, 8 pages.
(Continued)

*Primary Examiner* — Quynh-Nhu H. Vu
(74) *Attorney, Agent, or Firm* — Fish & Richardson P.C.

(57) ABSTRACT

The disclosure relates to a needle interface for connecting a hollow needle having a proximal tip to a medicament reservoir, the needle interface comprising an inner ring fixed to a reservoir wall of the reservoir and an outer ring attachable to the needle, wherein one of the inner ring and the outer ring comprises at least one magnet and wherein the other one of the inner ring and the outer ring comprises a magnetisable material or a magnet.

19 Claims, 4 Drawing Sheets

(51) Int. Cl.
*A61M 5/145* (2006.01)
*A61J 1/20* (2006.01)
*A61M 5/34* (2006.01)

(52) U.S. Cl.
CPC .............. *A61J 1/2013* (2015.05); *A61M 5/34* (2013.01); *A61M 5/145* (2013.01); *A61M 2005/14506* (2013.01); *A61M 2205/0272* (2013.01); *A61M 2205/8206* (2013.01)

(58) Field of Classification Search
CPC .. A61M 39/10; A61M 39/1011; A61M 39/20; A61M 2039/1033; A61M 2039/1077; A61M 5/427; A61M 2209/045; A61M 5/46; A61J 1/1475
See application file for complete search history.

(56) References Cited

U.S. PATENT DOCUMENTS

| | | | |
|---|---|---|---|
| 6,652,540 B1 * | 11/2003 | Cole | A61B 17/0057 128/898 |
| 7,255,682 B1 * | 8/2007 | Bartol, Jr. | A61M 5/158 604/116 |
| 7,794,451 B1 * | 9/2010 | Chuter | A61M 39/0208 600/30 |
| 8,171,938 B2 * | 5/2012 | Bengtson | A61M 39/0208 128/899 |
| 9,662,440 B2 * | 5/2017 | Yodfat | A61M 5/14232 |
| 2008/0039820 A1 * | 2/2008 | Sommers | A61M 39/0208 604/539 |
| 2008/0215035 A1 * | 9/2008 | Yodfat | A61M 5/14232 604/513 |
| 2015/0182453 A1 * | 7/2015 | Stinchcomb | A61K 9/0021 604/506 |
| 2016/0331937 A1 * | 11/2016 | Teoh | A61M 39/06 |
| 2017/0224912 A1 * | 8/2017 | Yodfat | A61M 5/14232 |

OTHER PUBLICATIONS

International Preliminary Report on Patentability in International Application No. PCT/EP2015/079608, dated Jun. 20, 2017, 6 pages.

* cited by examiner

NEEDLE INTERFACE

CROSS-REFERENCE TO RELATED APPLICATIONS

This application is a U.S. national stage application under 35 USC § 371 of International Application No. PCT/EP2015/079608, filed on Dec. 14, 2015, which claims priority to European Patent Application No. 14199393.1, filed on Dec. 19, 2014, the entire contents of which are incorporated herein by reference.

TECHNICAL FIELD

The disclosure relates to a needle interface for connecting a hollow needle having a proximal tip to a medicament reservoir.

BACKGROUND

A drug delivery device may include a medicament reservoir which must be kept sterile prior to use. The reservoir may be connected to a needle by piercing a wall of the reservoir with the needle. In some instances the needle may be attached to the reservoir by a needle interface. However, a connection between the needle and a flexible reservoir wall may be difficult to establish and maintain.

SUMMARY

The present disclosure provides an improved needle interface.

Exemplary embodiments of the disclosure are given in the dependent claims.

According to the disclosure a needle interface for connecting a hollow needle having a proximal tip to a medicament reservoir comprises an inner ring fixed to a reservoir wall of the reservoir and an outer ring attachable or attached to the needle, wherein one of the inner ring and the outer ring comprises at least one magnet and wherein the other one of the inner ring and the outer ring comprises a magnetisable material or a magnet.

The two rings form a needle channel through which the needle can pierce a reservoir wall of the reservoir and are arranged to magnetically attract each other thereby defining and maintaining the needle in position within the reservoir.

In an exemplary embodiment, the magnetisable material of the inner ring is embedded within a cladding comprising or consisting of a bio compatible and/or drug compatible material. This prevents the magnetisable material or the magnet within the inner ring from contaminating the medicament within the reservoir.

In an exemplary embodiment, the inner ring is embedded in the reservoir wall, e. g. the reservoir wall may comprise at least two layers sealed to each other wherein the inner ring would be positioned between two of these layers thus securing the inner ring to the reservoir wall.

In another exemplary embodiment, the inner ring is glued to an inner surface of the reservoir wall with a bio-compatible and/or drug-compatible adhesive thus securing the inner ring to the reservoir wall.

In an exemplary embodiment, the cladding consists of the same material as the reservoir wall, e.g. Ethylenvinylacetat. This material would allow for heat sealing the inner ring to the reservoir wall.

In an exemplary embodiment, the inner ring exhibits a thickness at least equal to a length of the needle proximally from the outer ring less a thickness of the reservoir wall such that the proximal tip does not protrude the inner ring when inserted into the reservoir.

In an exemplary embodiment, the inner ring comprises one or more flow channels which may be directed substantially transversally relative to a central bore in which the proximal tip is locatable. Providing multiple flow channels allows for fluidly connecting the needle to multiple positions on the circumferential surface of the inner ring thereby ensuring that the reservoir is more completely emptied as it may collapse around the inner ring. In an exemplary embodiment the flow channels extend radially from the central bore.

In another exemplary embodiment, the inner ring comprises a protective cage extending in the proximal direction, wherein a sum of a thickness of the inner ring and a length of the protective cage at least equal a length of the needle proximally from the outer ring less a thickness of the reservoir wall such that the proximal tip does not protrude the protective cage when inserted into the reservoir.

In an exemplary embodiment, the needle is arranged slidable with respect to the outer ring. In particular a magnetisable fixation ring may be disposable over the needle, wherein the fixation ring is axially fixable to the needle in at least one direction thus limiting the length of the needle capable of entering the reservoir.

In an exemplary embodiment, the fixation ring comprises one or more resilient arms adapted to engage into one of a series of recesses arranged on an outer surface of the needle in order to allow axially arresting the needle with respect to the fixation ring.

In an exemplary embodiment, one of the recesses near the proximal tip is adapted to lock the resilient arm such that the proximal tip is covered by the fixation ring. Hence, the risk for needle stick injuries is mitigated.

In an exemplary embodiment, the needle interface is part of a medicament reservoir for storing a medicament, comprising a flexible reservoir wall.

In an exemplary embodiment, a drug delivery device is provided comprising:

a pump for pumping a medicament from a medicament reservoir to a nozzle, and a hollow needle having a proximal tip adapted to be connected to the medicament reservoir.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

Figure 1:
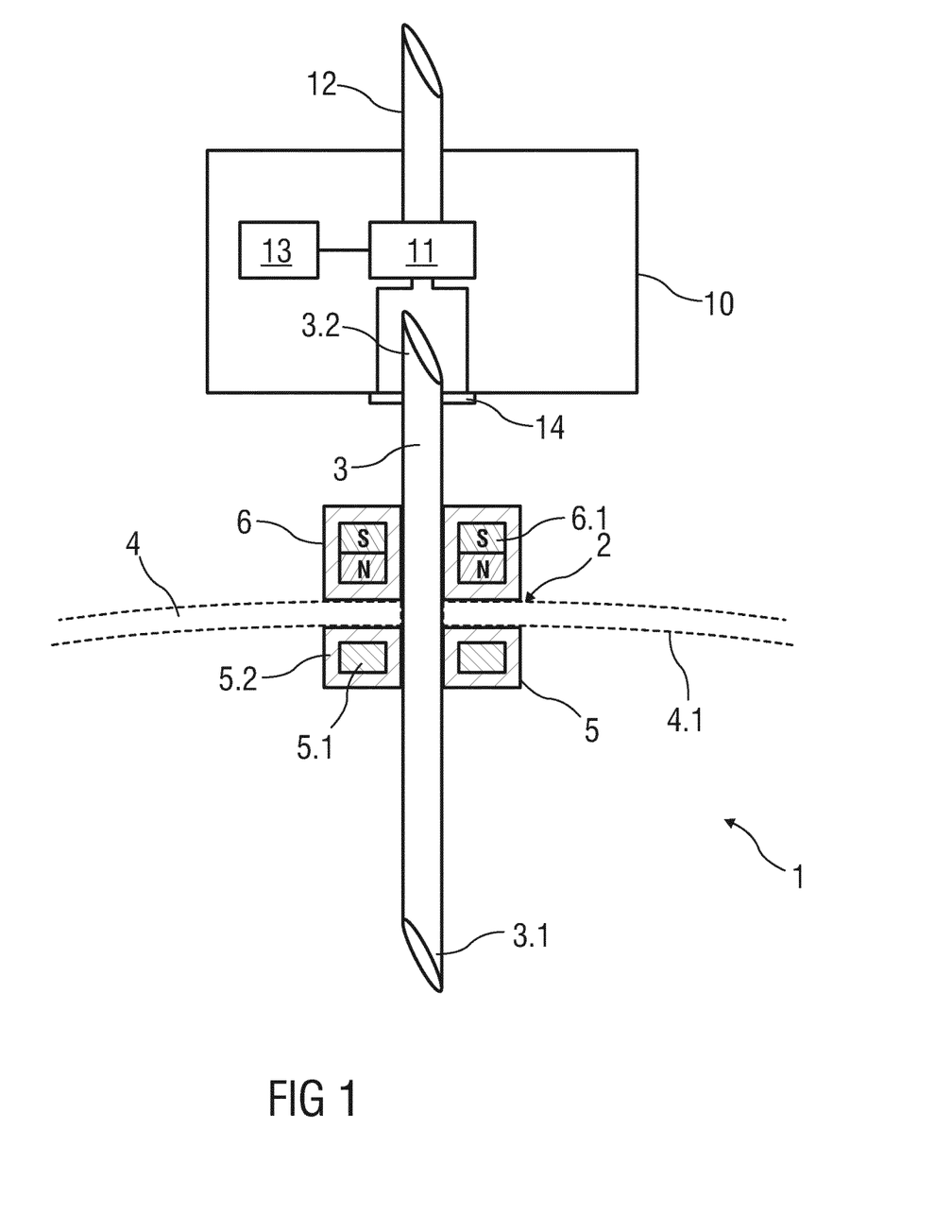
FIG. 1 is a schematic view of an exemplary embodiment of a medicament reservoir with a needle interface and a needle.

FIG. 1 is a schematic view of an exemplary embodiment of a medicament reservoir 1 with a needle interface 2 and a hollow needle 3, e.g. a hypodermic injection needle or a needle for connecting a drug delivery device 10 to the reservoir 1. The drug delivery device may comprise a pump 11 for pumping a medicament from the medicament reservoir 1 to a nozzle 12, e.g. a hypodermic needle. In an exemplary embodiment an energy source 13, e.g. a battery or a spring may be provided for powering the pump 11. The needle 3 comprises a proximal tip 3.1 adapted to penetrate a reservoir wall 4 of the reservoir 1 which may be a flexible reservoir. In an exemplary embodiment, the needle 3 may comprise a distal tip 3.2 adapted to pierce a septum 14 or membrane of the drug delivery device 10 in order to be connected to the pump 11. The needle 3 can be arranged such that the distal tip 3.2 may be used for piercing the reservoir wall 4 and the proximal tip 3.1 for piercing the septum 14 or membrane. In other exemplary embodiments the needle 3 may not comprise a distal tip but be permanently or releasably connected to the pump 11 in a different way. The needle interface 2 comprises an inner ring 5, e.g. a rigid ring, arranged within the reservoir 1, i.e. on an inner surface 4.1 of the reservoir wall 4. The inner ring 5 comprises a magnetisable material 5.1, i.e. a material that can be attracted by a magnet, e.g. a ferromagnetic or ferromagnetic material such as iron and/or nickel. The needle 3 comprises an attached outer ring 6 comprising at least one magnet 6.1, e.g. a permanent magnet or a solenoid, which may be coupled to an energy source, e.g. the energy source 13 of the drug delivery device 10. The outer ring 6 circumferentially surrounds a section of a shaft of the needle 3 and holds the needle in place when attached to the inner ring 5 on the reservoir 1 thereby holding the reservoir wall 4 between the inner ring 5 and the outer ring 6 and allowing the proximal tip 3.1 of the needle 3 to pierce the reservoir wall 4 through the inner ring 5 and the outer ring 6. The magnetisable material 5.1 of the inner ring 5 can be embedded within a cladding 5.2 comprising or consisting of a bio compatible and/or drug compatible material. This prevents the magnetisable material 5.1 from contaminating the medicament within the reservoir 1.

The outer ring 6 and the needle 3 may be reusable.

In an alternative embodiment the inner ring 5 may be embedded in the reservoir wall 4, e. g. the reservoir wall 4 may comprise at least two layers sealed to each other wherein the inner ring 5 would be positioned between two of these layers. In another alternative embodiment the inner ring 5 may be glued to the inner surface 4.1 with a bio-compatible and/or drug-compatible adhesive. In an exemplary embodiment the cladding 5.2 of the inner ring 5 can consist of the same material as the reservoir wall 4, e. g. Ethylenvinylacetat. This material would allow for heat sealing the inner ring 5 to the reservoir wall 4.

Figure 2:
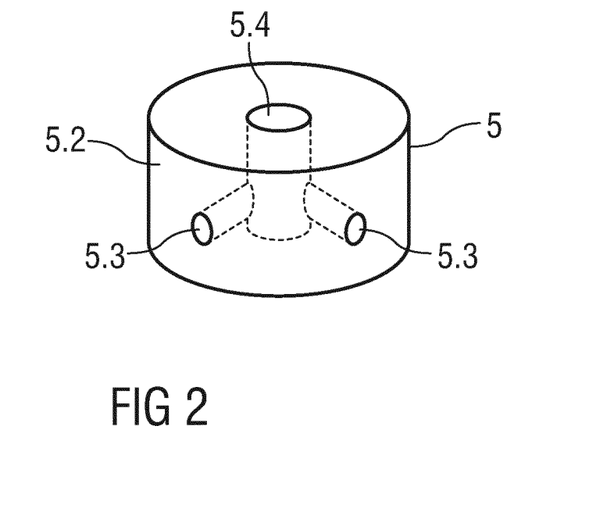
FIG. 2 is a schematic view of another exemplary embodiment of an inner ring of the needle interface.

FIG. 2 is a schematic view of another exemplary embodiment of the inner ring 5, wherein the magnetisable material 5.1 is not shown for clarity. Other than in the embodiment of FIG. 1, where the proximal tip 3.1 protrudes beyond the inner ring 5 into the reservoir 1 with the risk that the sharp proximal tip 3.1 could damage the reservoir 1 as it collapses, in the embodiment of FIG. 2 the inner ring 5 is adapted to protect the reservoir 1 from damage by the proximal tip 3.1. For this purpose, the inner ring 5 exhibits a thickness at least equal to the length of the needle 3 proximally from the outer ring 6 less a thickness of the reservoir wall 4 such that the proximal tip 3.1 does not protrude the inner ring 5 when inserted into the reservoir 1. In order to ensure uninterrupted fluid flow from the reservoir 1 to the needle 3, the inner ring 5 may comprise one or more flow channels 5.3 which may be directed substantially transversally relative to a central bore 5.4 in which the proximal tip 3.1 is located or locatable. In particular the flow channels 5.3 may extend radially from the central bore 5.4. Providing multiple flow channels 5.3 allows for fluidly connecting the needle 3 to multiple positions on the circumferential surface of the inner ring 5 thereby ensuring that the reservoir 1 is more completely emptied as it may collapse around the inner ring 5. In alternative exemplary embodiments, the flow channels 5.3 could extend in different directions.

Figure 3:
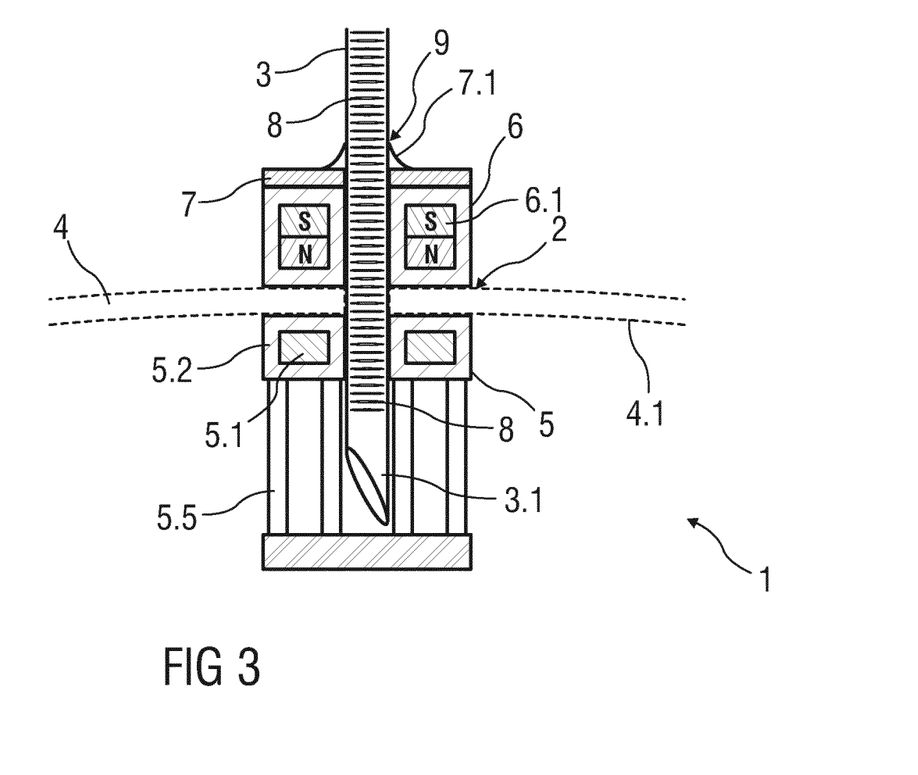
FIG. 3 is a schematic view of yet another exemplary embodiment of a medicament reservoir with a needle interface and a needle with a one-way clutch mechanism.

FIG. 3 is a schematic view of yet another exemplary embodiment of a medicament reservoir 1 with a needle interface 2 and a needle 3. The needle 3 comprises a proximal tip 3.1 adapted to penetrate a reservoir wall 4 of the reservoir 1 which may be a flexible reservoir. The needle interface 2 comprises an inner ring 5, e.g. a rigid ring, arranged within the reservoir 1, i.e. on an inner surface 4.1 of the reservoir wall 4. The inner ring 5 comprises a magnetisable material 5.1, i.e. a material that can be attracted by a magnet, e.g. a ferromagnetic or ferromagnetic material such as iron and/or nickel. An outer ring 6 is attached to the needle 3, the outer ring 6 comprising at least one magnet 6.1, e.g. a permanent magnet or a solenoid, which may be coupled to an energy source, e.g. the energy source 13 of the drug delivery device 10. The outer ring 6 circumferentially surrounds a section of a shaft of the needle 3 and holds the needle in place when attached to the inner ring 5 on the reservoir 1 thereby holding the reservoir wall 4 between the inner ring 5 and the outer ring 6 and allowing the proximal tip 3.1 of the needle 3 to pierce the reservoir wall 4 through the inner ring 5 and the outer ring 6. The magnetisable material 5.1 of the inner ring 5 can be embedded within a cladding 5.2 comprising or consisting of a bio compatible and/or drug compatible material. This prevents the magnetisable material 5.1 from contaminating the medicament within the reservoir 1. In this embodiment the inner ring 5 comprises a protective cage 5.5 extending in the proximal direction, wherein a sum of a thickness of the inner ring 5 and a length of the protective cage 5.5 at least equal to a length of the needle 3 proximally from the outer ring 6 less a thickness of the reservoir wall 4 such that the proximal tip 3.1 does not protrude the protective cage 5.5 when inserted into the reservoir 1. Furthermore, the needle 3 is arranged slidable with respect to the outer ring 6. In order to establish a fluid communication between the needle 3 and the reservoir 1 the outer ring 6 is attached to the reservoir 1 opposite the inner ring 5 thereby forming a needle channel for the needle 3 which can then be inserted through the outer ring 6 and the inner ring 5. A magnetisable fixation ring 7 is disposed over the needle 3. The fixation ring 7 is axially fixed to the needle 3 in at least one direction thus limiting the length of the needle 3 capable of entering the reservoir 1.

In the embodiment of FIG. 3 the fixation ring 7 is arranged to limit the movement of the needle 3 in the direction towards the reservoir 1. For this purpose the fixation ring 7 comprises one or more resilient arms 7.1 disposed on a distal side of the fixation ring 7, substantially directed radially inwards when relaxed and adapted to engage into one of a series of recesses 8 arranged on an outer surface of the needle 3, each recess 8 aligned substantially transversally with respect to a longitudinal axis of the needle 3 and the series of recesses 8 disposed along an axial direction of the needle 3. The fixation ring 7 may thus be moved towards the proximal tip 3.1 but not away from it.

In an exemplary embodiment, the fixation ring 7 may be designed to move freely to a second position near the sharp proximal tip 3.1 and arrest there to act as a needle safety device covering the proximal tip 3.1 when the needle 3 is removed from the reservoir 1.

When the needle 3 is retracted, the fixation ring 7 is held against the outer ring 6 by the magnetic forces. The needle 3 slides back through the fixation ring 7 while the resilient arms 7.1 jump along the recesses 8 towards the proximal tip 3.1 until the resilient arms 7.1 lock into one of the recesses 8 near the sharp proximal tip 3.1. The fixation of the fixation ring 7 to the needle 3 is strong enough to overcome the magnetic forces for separating the fixation ring 7 from the outer ring 6. The proximal tip 3.1 is then covered by the fixation ring 7 (cf. FIG. 5).

The resilient arms 7.1 and the recesses 8 form a one-way clutch mechanism 9 ensuring that the needle 3 can be retracted through the fixation ring 7 but cannot be re-advanced into the reservoir 1.

Figure 4:
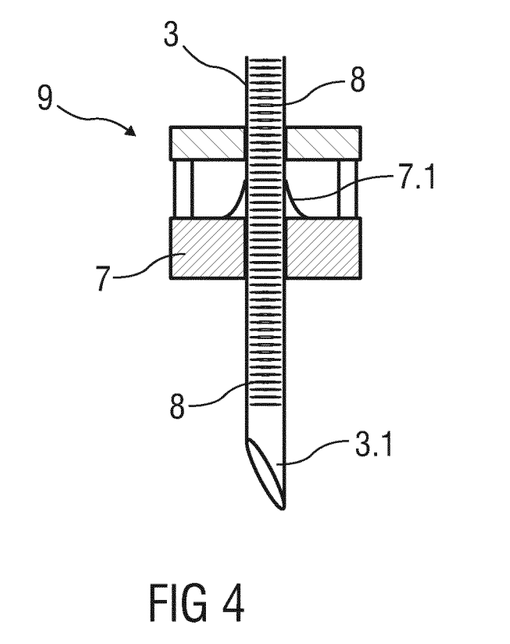
FIG. 4 is a schematic view of the one-way clutch mechanism with the needle extending from a fixation ring.
Figure 5:
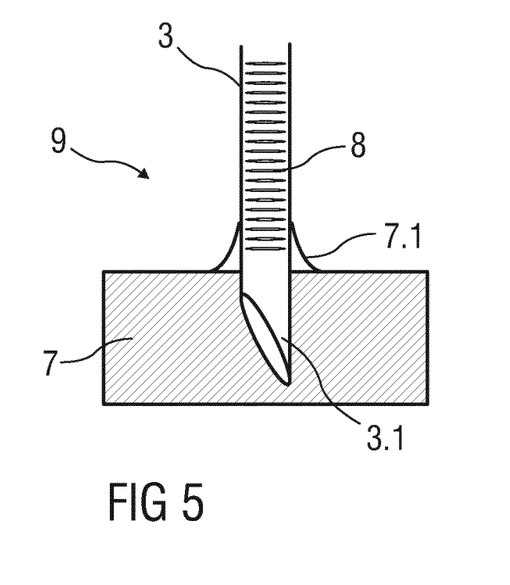
FIG. 5 is a schematic view of the one-way clutch mechanism with the needle covered by the fixation ring.

FIG. 4 is a schematic view of the one-way clutch mechanism 9 with the needle 3 extending from the fixation ring 7, e.g. prior to insertion into the reservoir 1. FIG. 5 is a schematic view of the one-way clutch mechanism 9 with the needle 3 covered by the fixation ring 7, e.g. after removal from the reservoir 1.

The protective cage 5.5 of FIG. 3 could also be combined with the embodiment of FIG. 1.

Arranging the magnetic outer ring 6 on the needle 3 and the magnetisable inner ring 5 within the reservoir 1 reduces costs as the inner ring 5 comprising the magnetisable material 5.1 is rather inexpensive compared to the magnet 6.1 within the magnetic outer ring 6.

All previously described embodiments can be modified by using an inner ring 5 with a magnet 6.1 and an outer ring 6 with a magnetisable material 5.1. Likewise, both the inner ring 5 and the outer ring 6 can comprise magnets. In the following, an example having an inner ring 5 with a magnet 6.1 and an outer ring 6 with a magnetisable material 5.1 is described.

Figure 6:
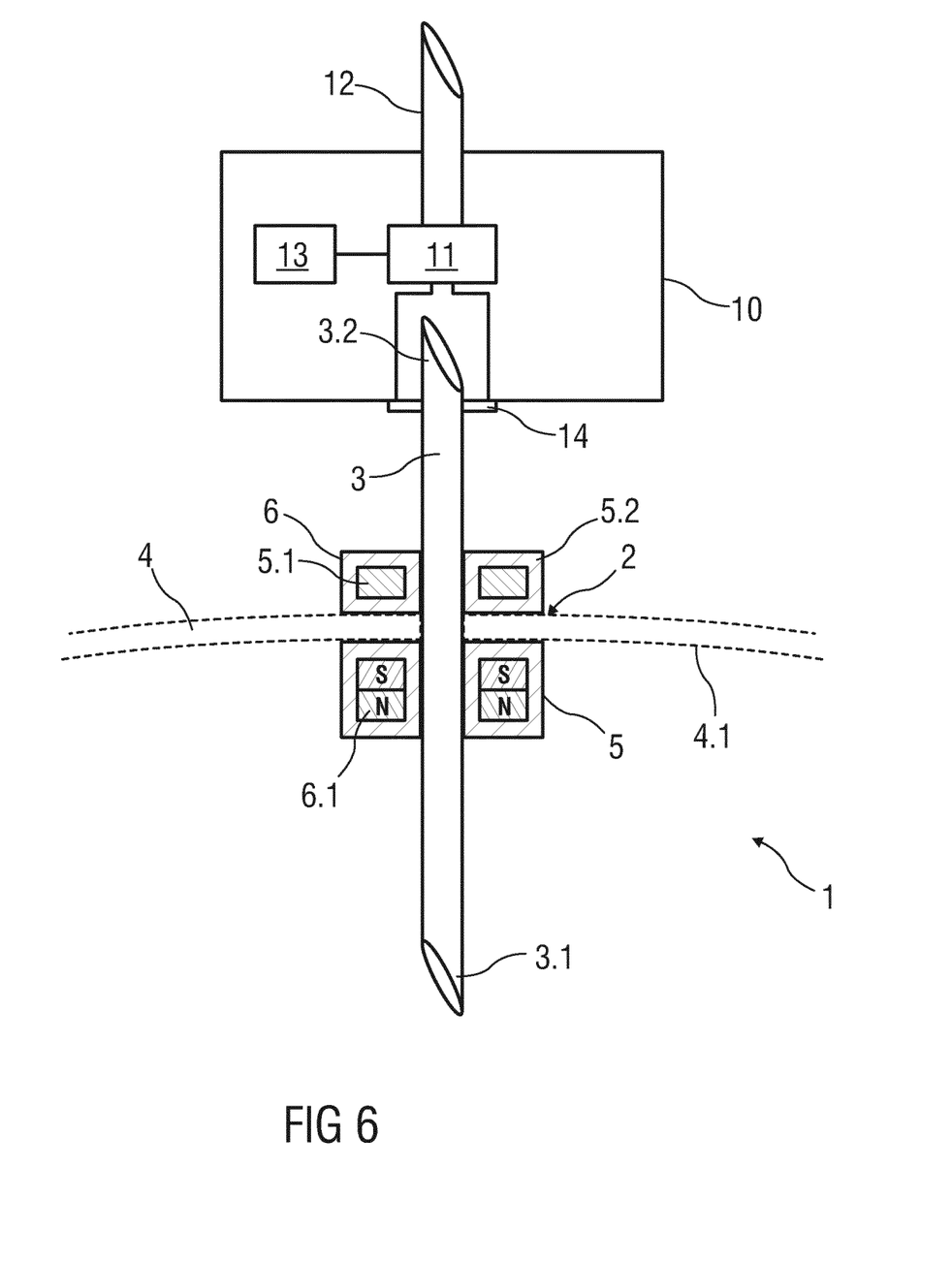
FIG. 6 is a schematic view of an exemplary embodiment of a medicament reservoir with a needle interface and a hollow needle.

FIG. 6 is a schematic view of an exemplary embodiment of a medicament reservoir 1 with a needle interface 2 and a hollow needle 3, e.g. a hypodermic injection needle or a needle for connecting a drug delivery device 10 to the reservoir 1. The drug delivery device may comprise a pump 11 for pumping a medicament from the medicament reservoir 1 to a nozzle 12, e.g. a hypodermic needle. In an exemplary embodiment an energy source 13, e.g. a battery or a spring may be provided for powering the pump 11. The needle 3 comprises a proximal tip 3.1 adapted to penetrate a reservoir wall 4 of the reservoir 1 which may be a flexible reservoir. The needle interface 2 comprises an inner ring 5, e.g. a rigid ring, arranged within the reservoir 1, i.e. on an inner surface 4.1 of the reservoir wall 4. The inner ring 5 comprises at least one magnet 6.1, e.g. a permanent magnet or a solenoid, which may be coupled to an energy source, e.g. the energy source 13 of the drug delivery device 10. The needle 3 comprises an attached outer ring 6 comprising a magnetisable material 5.1, i.e. a material that can be attracted by a magnet, e.g. a ferromagnetic or ferrimagnetic material such as iron and/or nickel. The outer ring 6 circumferentially surrounds a section of a shaft of the needle 3 and holds the needle in place when attached to the inner ring 5 on the reservoir 1 thereby holding the reservoir wall 4 between the inner ring 5 and the outer ring 6 and allowing the proximal tip 3.1 of the needle 3 to pierce the reservoir wall 4 through the inner ring 5 and the outer ring 6. The magnet 6.1 of the inner ring 5 can be embedded within a cladding 5.2 comprising or consisting of a bio compatible and/or drug compatible material. This prevents the magnet 6.1 from contaminating the medicament within the reservoir 1.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 reservoir
2 needle interface
3 needle
3.1 proximal tip
3.2 distal tip
4 reservoir wall
4.1 inner surface
5 inner ring
5.1 magnetisable material
5.2 cladding
5.3 flow channel
5.4 central bore
5.5 protective cage
6 outer ring
6.1 magnet
7 fixation ring
7.1 resilient arm
8 recess
9 one-way clutch mechanism
10 drug delivery device
11 pump
12 nozzle
13 energy source
14 septum

The invention claimed is:

1. A medical apparatus comprising:
a hollow needle having a proximal tip;
a medicament reservoir, wherein the proximal tip of the hollow needle is connected to the medicament reservoir;
an inner ring fixed to a reservoir wall of the reservoir and disposed within the reservoir; and
an outer ring attachable to the needle,
wherein one of the inner ring and the outer ring comprises at least one magnet, and wherein the other one of the inner ring and the outer ring comprises a magnetisable material or a magnet, and
wherein the reservoir wall is held between the inner ring and the outer ring by the outer ring circumferentially surrounding a section of a shaft of the needle and holding the needle in place when the needle is attached to the inner ring on the reservoir.

2. The medical apparatus according to claim 1, wherein the inner ring comprises the magnetisable material and the magnetisable material of the inner ring is embedded within a cladding comprising a bio-compatible material or a drug-compatible material.

3. The medical apparatus according to claim 2, wherein a material of the cladding comprises the same material as a material of the reservoir wall.

4. The medical apparatus according to claim 3, wherein the material of the cladding comprises Ethylenvinylacetat.

5. The medical apparatus according to claim 1, wherein the inner ring comprises the magnetisable material, and the magnetisable material of the inner ring is embedded within a cladding comprising a material that is bio-compatible and drug-compatible.

6. The medical apparatus according to claim 1, wherein the inner ring is within the reservoir.

7. The medical apparatus according claim 1, wherein the inner ring is glued to an inner surface of the reservoir wall with a bio-compatible adhesive or a drug-compatible adhesive.

8. The medical apparatus according to claim 1, wherein the inner ring is glued to an inner surface of the reservoir wall with an adhesive that is bio-compatible and drug-compatible.

9. The medical apparatus The needle interface according to claim 1, wherein the inner ring has a thickness at least equal to a length of the needle proximally from the outer ring, less a thickness of the reservoir wall.

10. The medical apparatus according to claim 9, wherein the inner ring comprises one or more flow channels.

11. The medical apparatus according to claim 10, wherein the one or more flow channels are directed substantially transversally relative to a central bore in which the proximal tip is locatable.

12. The medical apparatus according to claim 11, wherein the one or more flow channels extend radially from the central bore.

13. The medical apparatus according to claim 1, further comprising a protective cage attached to the inner ring and extending in a proximal direction, wherein a sum of a thickness of the inner ring and a length of the protective cage is at least equal to a length of the needle extending proximally from the outer ring less a thickness of the reservoir wall.

14. The medical apparatus according to claim 1, wherein the needle is configured to be slidable with respect to the outer ring.

15. The medical apparatus according to claim 14, wherein a magnetisable fixation ring is disposable over the needle, and the magnetisable fixation ring is axially fixable to the needle in at least one direction thus limiting a length of the needle capable of entering the reservoir.

16. The medical apparatus according to claim 15, wherein the magnetisable fixation ring comprises one or more resilient arms adapted to engage into one of a series of recesses arranged on an outer surface of the needle.

17. A medicament reservoir for storing a medicament, the medicament reservoir comprising:
a flexible reservoir wall; and
a needle interface comprising
an inner ring fixed to the flexible reservoir wall of the medicament reservoir and disposed within the medicament reservoir; and
an outer ring attachable to a needle,
wherein one of the inner ring and the outer ring comprises at least one magnet, and the other one of the inner ring and the outer ring comprises a magnetisable material or a magnet, and wherein the flexible reservoir wall is held between the inner ring and the outer ring by the outer ring circumferentially surrounding a section of a shaft of the needle and holding the needle in place when attached to the inner ring on the reservoir.

18. A drug delivery device comprising:
a medicament reservoir for storing a medicament, the medicament reservoir comprising:
a flexible reservoir wall; and
a needle interface comprising
an inner ring fixed to the flexible reservoir wall of the reservoir and disposed within the reservoir, and
an outer ring attachable to a needle,
wherein one of the inner ring and the outer ring comprises at least one magnet, and the other one of the inner ring and the outer ring comprises a magnetisable material or a magnet, and
wherein the flexible reservoir wall is held between the inner ring and the outer ring by the outer ring circumferentially surrounding a section of a shaft of the needle and holding the needle in place when attached to the inner ring on the reservoir; and
a pump for pumping a medicament from the medicament reservoir to a nozzle.

19. The drug delivery device of claim 18, further comprising a medicament disposed in the medicament reservoir, wherein the medicament comprises a pharmaceutically active compound.

* * * * *

UNITED STATES PATENT AND TRADEMARK OFFICE
CERTIFICATE OF CORRECTION

PATENT NO. : 10,471,206 B2
APPLICATION NO. : 15/536380
DATED : November 12, 2019
INVENTOR(S) : Marcus-Meinolf Dittrich It is certified that error appears in the above-identified patent and that said Letters Patent is hereby corrected as shown below:

In the Claims

Column 10, Line 48, Claim 1, after "and", delete "wherein"

Column 10, Line 65, Claim 4, delete "Ethylenvinylacetat." and insert -- Ethylenevinylacetate. --

Column 11, Line 6, Claim 7, after "according", insert -- to --

Column 11, Line 14, Claim 9, after "apparatus", delete "The needle interface"

Column 12, Line 6, Claim 17, after "comprising", insert -- : --

Signed and Sealed this
Fourth Day of February, 2020

Andrei Iancu
*Director of the United States Patent and Trademark Office*